(12) United States Patent
Beaujuge et al.

(10) Patent No.: US 8,865,916 B2
(45) Date of Patent: Oct. 21, 2014

(54) FUNCTIONALIZED DIAMOND NANOPARTICLES

(71) Applicants: Pierre M. Beaujuge, Thuwal (SA); Omar El Tall, Thuwal (SA); Inam U. Raja, Thuwal (SA)

(72) Inventors: Pierre M. Beaujuge, Thuwal (SA); Omar El Tall, Thuwal (SA); Inam U. Raja, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 13/935,508

(22) Filed: Jul. 4, 2013

(65) Prior Publication Data

US 2014/0012014 A1 Jan. 9, 2014

Related U.S. Application Data

(60) Provisional application No. 61/668,415, filed on Jul. 5, 2012.

(51) Int. Cl.
  *C07D 207/444* (2006.01)
  *C07D 209/58* (2006.01)
  *C01B 31/06* (2006.01)

(52) U.S. Cl.
  CPC ................ *C01B 31/065* (2013.01); *Y10S 977/753* (2013.01)
  USPC ........................... 548/548; 977/753

(58) Field of Classification Search
  None
  See application file for complete search history.

(56) References Cited

U.S. PATENT DOCUMENTS 8,679,859 B2 * 3/2014 Yan et al. ............ 436/518

OTHER PUBLICATIONS

Kruger, et al., J. Mat. Chem., 16:2322 (2006).*

* cited by examiner

*Primary Examiner* — Michael Barker
(74) *Attorney, Agent, or Firm* — Steptoe & Johnson LLP

(57) ABSTRACT

A diamond nanoparticle can be functionalized with a substituted dienophile under ambient conditions, and in the absence of catalysts or additional reagents. The functionalization is thought to proceed through an addition reaction.

13 Claims, 3 Drawing Sheets

FUNCTIONALIZED DIAMOND NANOPARTICLES

CLAIM OF PRIORITY

This application claims the benefit of prior U.S. Provisional Application No. 61/668,415, filed on Jul. 5, 2012, which is incorporated by reference in its entirety.

TECHNICAL FIELD

This invention relates to functionalized diamond nanoparticles and methods of making functionalized diamond nanoparticles.

BACKGROUND

Diamond materials have a range of physical properties that make them attractive for a variety of uses. Functionalization of these materials can allow the diamond materials to be used in a variety of applications.

SUMMARY

A diamond nanoparticle can be functionalized with a substituted dienophile under ambient conditions, and in the absence of catalysts or additional reagents. The functionalization is thought to proceed through a cycloaddition reaction, such as a Diels-Alder reaction, or by association with a reactive moiety, such as a dangling bond (unsatisfied valence).

In one aspect, a method of making a functionalized diamond nanoparticle includes exposing a diamond nanoparticle having surface diene moieties, nucleophilic moieties and/or dangling bonds to a dienophile to form a functionalized diamond nanoparticle product. Exposing the diamond nanoparticle to the dienophile can take place at about ambient conditions, for example, ambient temperature and/or ambient pressure. The method can be carried out in the absence of catalyst and additional reagents.

In certain embodiments, the dienophile can be a cyclic imide, a furan, a pyrrole, a thiophene, or a cyclic anhydride, for example, maleimide. In other embodiments, the dienophile can be an acyclic alkene.

In another aspect, a compound can have a structure of a formula (I):

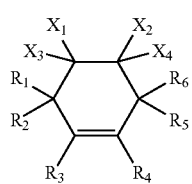

In formula (I), each of $R_1$, $R_2$, $R_3$, $R_4$, $R_5$, or $R_6$, independently, are hydrogen or carbon atoms of a diamond nanoparticle, no more than two of $R_1$, $R_2$, $R_3$, $R_4$, $R_5$, or $R_6$ being hydrogen, In formula (I), each of $X_1$ and $X_2$, independently, can be an electron withdrawing group, and In formula (I), each of $X_3$ and $X_4$, independently, can be hydrogen, alkyl, an ester, amide, nitro, or nitrile or $X_3$ and $X_4$ together form a bond.

In another aspect, a compound can have formula (II):

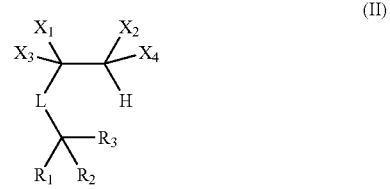

In formula (II), each of $R_1$, $R_2$, or $R_3$, independently, are hydrogen or carbon atoms of a diamond nanoparticle, no more than one of $R_1$, $R_2$, or $R_3$, being hydrogen.

In formula (II), each of $X_1$ and $X_2$, independently, is an electron withdrawing group.

In formula (II), each of $X_3$ and $X_4$, independently, is hydrogen, alkyl, an ester, amide, nitro, or nitrile or $X_3$ and $X_4$ together form a bond.

In formula (II), L is an oxo, thio or amino terminated linking group, or a bond, the linking group being a C2-C16 alkylene, arylene or aralkylene group, the oxo, thio or amino group forming a bond with the carbon substituted by $X_1$ and $X_3$.

In certain embodiments, in formula (I) or formula (II), $X_3$ and $X_4$ together can form a bond.

In certain embodiments, in formula (I) or formula (II), each of $X_3$ and $X_4$ can be hydrogen.

In certain embodiments, in formula (I) or formula (II), the electron withdrawing group can be an ester, amide, nitro, or nitrile.

In certain embodiments, in formula (I) or formula (II), each of $X_1$ and $X_2$ can be an ester or amide.

In certain embodiments, in formula (I) or formula (II), each of $X_1$ and $X_2$ can be an ester or amide and together can form a 5- to 8-membered ring.

In certain embodiments, in formula (I), 2, 3, 4, 5, or 6 of $R_1$-$R_6$ can be carbon atoms of the diamond nanoparticle.

In certain embodiments, in formula (I) or formula (II), the compound is a maleimide adduct of a diamond nanoparticle.

Other features or advantages will be apparent from the following detailed description of several embodiments, and also from the appended claims.

DETAILED DESCRIPTION

Figure 1A:
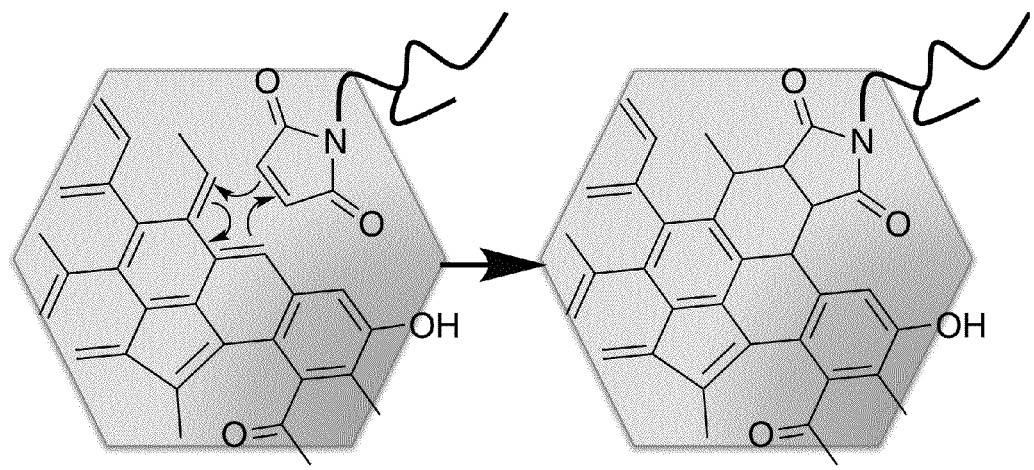
FIGS. 1A and 1B is a schematic diagram depicting various functionalization paths of maleimide onto lightly-graphitized DNPs (GDNPs).

With their wide range of physical properties (e.g. high mechanical and chemical resistance, variable optical "band-gap", high thermal conductivity, etc.), diamond materials introduce a number of opportunities at the nanoscale. Of all useful sources of diamond nanomaterials, detonation diamond nanoparticles (DDNPs) provide high specific surface areas (300-400 $m^2 \cdot g^{-1}$) with achievable nanoparticle sizes as low as 4-5 nm. The ability to prepare DDNPs in this size-range has extended the study and application of diamond in the field of nanomedicine, as a drug-delivery agent in particular. In principle, DDNPs represent a readily accessible and biocompatible platform for biomedical applications.

DDNPs are also known to offer a convenient platform for further functionalizations with a broad range of substituents, including aliphatic and polar/ionic organic groups. A number of contributions have reported on the substitution of DDNPs with functional substituents such as small organic molecules, biomolecules, peptides, metals, dyes, oligomers, polymers. See, for example, Liang, Y.; Meinhardt, T.; Jane, G.; Ozawa, M.; Vrdoljak, P.; Scholl, A.; Reinert, F.; Krueger, A., Deagglomeration and surface modification of thermally annealed nanoscale diamond. *Journal of colloid and interface science* 2011, 354 (1), 23-30; Barras, A.; Lyskawa, J.; Szuner-its, S.; Woisel, P.; Boukherroub, R., Direct Functionalization of Nanodiamond Particles Using Dopamine Derivatives. *Langmuir: the ACS journal of surfaces and colloids* 2011, 27 (20), 12451-12457; Krueger, A.; Stegk, J.; Liang, Y.; Lu, L.; Jarre, G., Biotinylated nanodiamond: simple and efficient functionalization of detonation diamond. Langmuir: the ACS journal of surfaces and colloids 2008, 24 (8), 4200-4; Kruger, A.; Liang, Y.; Jane, G.; Stegk, J., Surface functionalisation of detonation diamond suitable for biological applications. *Journal of Materials Chemistry* 2006, 16 (24), 2322-2328; A. M. Panich, A. A., A. I. Shames, V. Yu. Osipov, A. E. Aleksen-skiy and A. Ya Vul, Proton magnetic resonance study of diamond nanoparticles decorated by transition metal ions *Journal of Physics D: Applied Physics* 2011, 44; Hens, S. C.; Cunningham, G.; Tyler, T.; Moseenkov, S.; Kuznetsov, V.; Shenderova, O., Nanodiamond bioconjugate probes and their collection by electrophoresis. *Diamond and Related Materials* 2008, 17 (11), 1858-1866; Chang, I. P.; Hwang, K. C.; Ho, J. A.; Lin, C. C.; Hwu, R. J.; Horng, J. C., Facile surface functionalization of nanodiamonds. *Langmuir: the ACS journal of surfaces and colloids* 2010, 26 (5), 3685-9; Behler, K. D.; Stravato, A.; Mochalin, V.; Korneva, G.; Yushin, G.; Gogotsi, Y., Nanodiamond-Polymer Composite Fibers and Coatings. ACS Nano 2009, 3 (2), 363-369; or Zhang, Q.; Mochalin, V. N.; Neitzel, I.; Knoke, I. Y.; Han, J.; Klug, C. A.; Zhou, J. G.; Lelkes, P. I.; Gogotsi, Y., Fluorescent PLLA-nanodiamond composites for bone tissue engineering. *Biomaterials* 2011, 32 (1), 87-94, each of which is incorporated by reference in its entirety. It is worth noting that their surface can also be tuned by exposure to high temperatures and under specific gas or vacuum atmospheres. Thus, short chemical functionalities such as —H, —OH—COOH, —$NH_2$, or —C═C groups can be selectively produced at the surface of DDNPs. These protocols can typically be used as leverages for further functionalizations with specific organic molecules (e.g. by esterification, amidation, silanization, C—C bonding, etc.), and these processes are likely to occur in very specific reaction conditions. See, for example, Krueger, A.; Boedeker, T., Deagglomeration and functionalisation of detonation nanodiamond with long alkyl chains. *Diamond and Related Materials* 2008, 17 (7-10), 1367-1370; Mochalin, V. N.; Neitzel, I.; Etzold, B. J.; Peterson, A.; Palmese, G.; Gogotsi, Y., Covalent incorporation of aminated nanodiamond into an epoxy polymer network. *ACS Nano* 2011, 5 (9), 7494-502; Chang, Y.-R.; Lee, H.-Y.; Chen, K.; Chang, C.-C.; Tsai, D.-S.; Fu, C.-C.; Lim, T.-S.; Tzeng, Y.-K.; Fang, C.-Y.; Han, C.-C.; Chang, H.-C.; Fann, W., Mass production and dynamic imaging of fluorescent nanodiamonds. *Nat Nano* 2008, 3 (5), 284-288; Krueger, A.; Ozawa, M.; Jarre, G.; Liang, Y.; Stegk, J.; Lu, L., Deagglomeration and functionalisation of detonation diamond. *physica status solidi (a)* 2007, 204 (9), 2881-2887; or Liang, Y.; Meinhardt, T.; Jane, G.; Ozawa, M.; Vrdoljak, P.; Scholl, A.; Reinert, F.; Krueger, A., Deagglomeration and surface modification of thermally annealed nanoscale diamond. *Journal of colloid and interface science* 2011, 354 (1), 23-30, each of which is incorporated by reference in its entirety. To date, the covalent attachment of organic molecules represents the most effective route to the functionalization of DDNPs with drugs and other useful functional groups, although these surface reactions are often temperature-dependent, relatively tedious, time-consuming, and often require the use of a catalyst or coupling agent.

A recent report described the functionalization of carbon nanotubes (CNTs) by Diels-Alder cycloaddition. Cycloaddition reactions allow facile C—C direct couplings between "donor" and "acceptor" partner molecules or functionalities, such as "dienes" and "dienophiles". In this case, the $sp^2$-like graphitic surface of CNTs can be seen as providing the "diene" components that react in cycloaddition with the C═C functionality of a molecular "dienophile". See, for example, Munirasu, S.; Albuerne, J.; Boschetti-de-Fierro, A.; Abetz, V., Functionalization of Carbon Materials using the Diels-Alder Reaction. *Macromolecular Rapid Communications* 2010, 31 (6), 574-579, which is incorporated by reference in its entirety. In principle, the reverse case where the CNT surface would provide the "dienophile" components can also be possible. Importantly, cycloadditions may not require catalysts or additional reagents to be added to the reaction mixture, may not generate reaction byproducts, may be achieved under mild temperature conditions, and are accomplished in a one-step process.

Figure 1B:
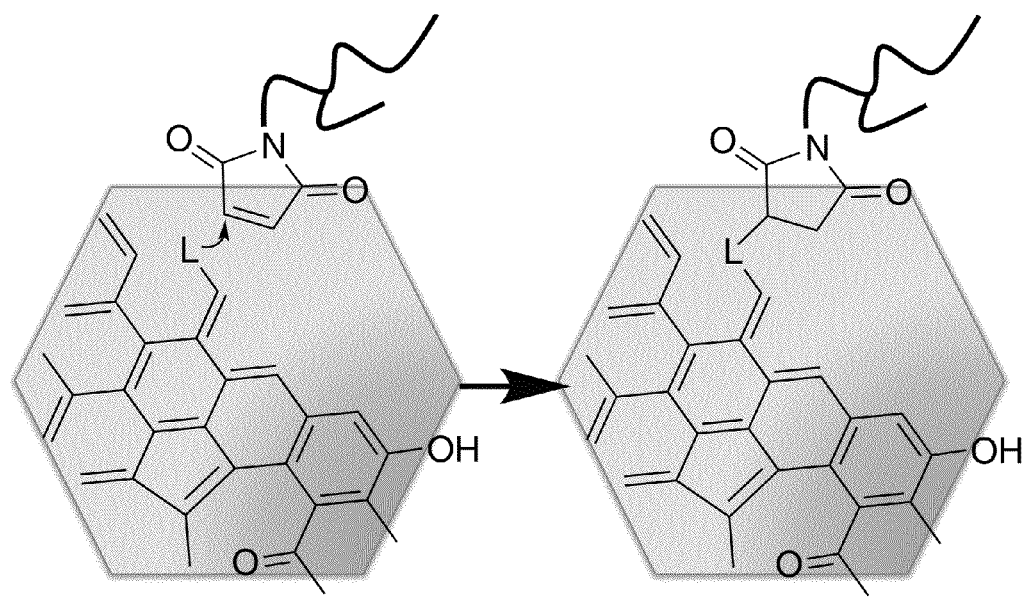

Similarly, it is expected that reactive surface diene moieties can be present at the surface of DDNPs, and that their density can be controlled by thermal annealing treatments. On this basis, DDNP surfaces may be reactive towards a known molecular dienophile such as "maleimide". This imide can be synthesized from its commercial anhydride precursor, and offers a readily accessible reactive C═C functionality for Diels-Alder cycloadditions. A controlled thermal annealing treatment of DDNPs enhances the reactivity of the nanoparticles towards the molecular dienophile "maleimide". Interestingly, such DDNPs react with maleimide derivatives by simple exposure of the two partners in various organic solvents. FIG. 1A provides a schematic representation of the expected functionalization route of maleimide onto "graphitized" DNPs (GDNPs); since a certain degree of graphitization can be expected to occur during the thermal treatment of the DDNPs. FIG. 1B provides a schematic representation of the expected functionalization route of maleimide onto "graphitized" DNPs (GDNPs) via a nucleophilic addition reaction with a surface group in the GDNPs. In FIG. 1B, L can be a dangling bond, hydroxy, thiol or amino-terminated group prior to reaction.

Under the assumption of a cycloaddition reaction, the resulting cyclized adduct can have a formula (I):

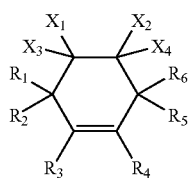
(I)

In the compound, each of $R_1$, $R_2$, $R_3$, $R_4$, $R_5$, or $R_6$, independently, are hydrogen or carbon atoms of a diamond nanoparticle, no more than two of $R_1$, $R_2$, $R_3$, $R_4$, $R_5$, or $R_6$ being hydrogen. In preferred embodiments, 2, 3, 4, 5, or 6 of $R_1$-$R_6$ are carbon atoms of the diamond nanoparticle. A majority (more than 60%, 70%, 80%, 90% or more) of the carbon atoms of the diamond nanoparticle can be an sp$^3$ carbon.

In the compound, each of $X_1$ and $X_2$, independently, is an electron withdrawing group. The electron withdrawing group can be an ester, amide, nitro, or nitrile. When each of $X_1$ and $X_2$ are ester or amide, $X_1$ and $X_2$ together can form a 5- to 8-membered ring, for example, an anhydride, an imide, a furan, a pyrrole, or a thiophene. The ester or amide can be an alkyl ester or alkyl amide having one or more optional substituents selected from halo, hydroxy, amino, ester, or amide.

In the compound, each of $X_3$ and $X_4$, independently, is hydrogen, alkyl, an ester, amide, nitro, or nitrile or $X_3$ and $X_4$ together form a bond. In certain embodiments, $X_3$ and $X_4$ together form a bond. In other embodiments, each of $X_3$ and $X_4$ are hydrogen.

For example, the compound can be a maleimide adduct of a diamond nanoparticle or a "succinimide"-modified diamond nanoparticle—thus accounting for the change in bond order as the maleimide moiety reacts.

The compound can be prepared via a cycloaddition reaction according to the Scheme 1:

Scheme 1

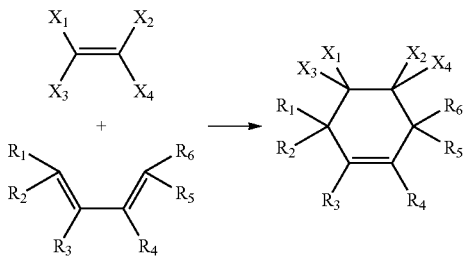

Under the assumption of a nucleophilic addition reaction, the resulting cyclized adduct can have a formula (II):

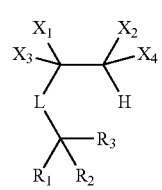
(II)

In formula (II), each of $R_1$, $R_2$, or $R_3$, independently, are hydrogen or carbon atoms of a diamond nanoparticle, no more than one of $R_1$, $R_2$, or $R_3$, being hydrogen. For example, L is a linking functionality on a surface of the diamond nanoparticle. In formula (II), L is a bond, oxo, thio or amino-terminated linking group, the linking group being a C2-C16 alkylene, arylene or aralkylene group, the oxo, thio or amino group forming a bond with the carbon substituted by $X_1$ and $X_3$. For example, L, prior to reaction, can be a surface thiol group, such as a thioalkyl or thiophenol group. In another example, L can be a radical or dangling bond.

In formula (II), each of $X_1$, $X_2$, $X_3$ and $X_4$, independently, can be as described above for formula (I).

The compound can be prepared via a nucleophilic addition reaction according to the Scheme 2:

Scheme 2

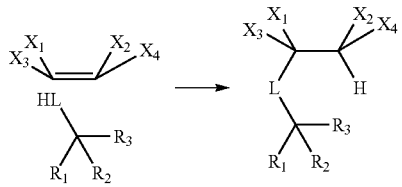

"Alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Halogen" or "halo" may be fluoro, chloro, bromo or iodo.

The alkyl can optionally include one or more carbon-carbon double bonds. "Alkenyl" refers to an olefinically unsaturated branched or linear group having at least one double bond. Alkenyl groups include, but are not limited to, 1-propenyl, 2-propenyl, 1,3-butadienyl, 1-butenyl, hexenyl, pentenyl, hexenyl, heptenyl, octenyl and the like.

This novel approach to the substitution of diamond nanoparticles with organic molecules can have a critical impact in the preparation of functional nanodiamonds for biological and biomedical applications, as the room-temperature reaction occurs without the need for additional reagents/catalysts, and occurs in a variety of common solvents. This is expected to allow for the substitution of DNA, RNA, proteins, drugs, and any other temperature-sensitive molecular species, onto nanodiamonds. In principle, the use of maleimide derivatives appended with polar/ionic solubilizing groups (e.g. sulfonates, phosphonates, carboxylates, etc.) should account for the solubility of the resulting nanodiamonds in aqueous solvents, thus potentially providing improved integration in biological systems, including human cells.

The absence of byproducts generated during the course of the functionalization can represent a tremendous advantage over most other functionalization approaches. This parameter considerably simplifies the purification protocol, and allows a rapid isolation of the functionalized nanodiamonds.

The covalent character of the bonding interaction expected between the GDNPs and the organic substituents makes the resulting organic hybrid a potentially highly stable system in both environmental and biological conditions.

The spontaneous and direct functionalization of organic molecules on nanodiamonds is particularly uncommon, and non trivial to achieve. For example, arylated diazonium molecules have been described as spontaneously reacting with hydrogenated diamond nanoparticles, (see, for example, Zhong, Y. L.; Loh, K. P.; Midya, A.; Chen, Z.-K., Suzuki Coupling of Aryl Organics on Diamond. *Chemistry of Materials* 2008, 20 (9), 3137-3144) however the hydrogenation of diamond nanomaterials involves experimental hazards associated to the use of an explosive gas, and diazonium compounds are themselves explosive and may not be manipulated in large quantities. On this basis, the functionalizations with maleimide and potentially with other dienophiles, represents a non-hazardous alternative to the reductive addition of diazonium derivatives on hydrogenated diamond.

One important aspect of this discovery is that nanodiamonds subjected to a careful annealing treatment are more reactive towards the dienophile maleimide. This could be due to the removal of the polar groups (e.g. hydroxyls, carbonyls, lactones, anhydrides, etc.) from the surface of the DDNPs, along with the appearance of new diene moieties at the surface, and/or that of dangling bond moieties. In contrast, detonation diamonds (DDNPs) not subjected to this annealing treatment may not be as readily functionalized by the dienophile.

The potential ability to attach biological molecules and polymers at room-temperature on nanodiamonds, without generating byproducts, and without the use of additional reagents/catalysts, gives access to nanomaterials that can be used and applied readily. Another potential advantage of the functionalization approach is the possibility of a retroactive reaction triggered at higher temperature, and leading to the removal of the maleimide functional substituent (by retro-Diels-Alder).

Pharmaceutical industries and start-ups of biotechnology are likely to be interested in the use of these facile functionalizations as nanodiamonds become a viable drug delivery agent, and/or an effective platform in nanomedicine in general. The potential of diamond as a biocompatible nanomaterial, with considerable stability and resistance in biological systems, make it a primary candidate in the field of nanotechnologies for therapeutic applications.

In parallel, the ability to functionalize nanodiamonds with a wide variety of substituents is expected to allow for nanomaterials that can be solution-processed in thin-films for use as coatings (including wear-protection layers). The nanodiamond cores may have varying band-gaps, thus tunable electronic and optical properties, as may be required for smart coating technologies. These may also find applications as lubricants, with potentially improved lubricating properties based on the nature of the functional groups appended to the nanodiamonds. In these areas, the ease of access of functional nanomaterials based on diamond may allow for large-scale and cost-effective productions.

In the following sections, the spontaneous character of this facile DDNP functionalization approach is highlighted using a number of characterization techniques in support of the findings: Raman, FTIR, solid-state NMR, elemental analysis, XPS, HRTEM-EELS. Some of these results are shown below. The useful control experiments were also used to confirm the findings.

DDNP Preparation and Functionalization—

Figure 2:
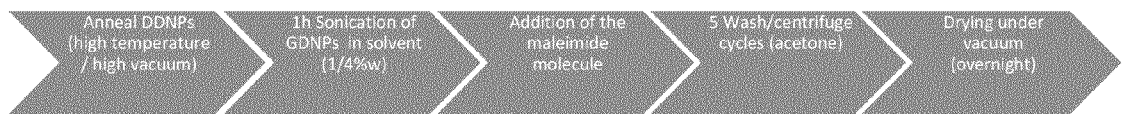
FIG. 2 is a schematic depicting a general procedure for the preparation of DNPs functionalized with maleimide derivatives.

Commercial DDNPs were subjected to various annealing temperatures and times of exposure, under vacuum, in order to trigger their surface "graphitization". Raman was used to follow the evolution of the D and G bands with respect to annealing, thus accounting for the degree of induced graphitization ($sp^2$ carbons) and for the loss of oxygen-containing surface groups. A 2-ethylhexyl-substituted derivative of maleimide was synthesized, and used for the functionalization of the "graphitized" diamond nanoparticles (GDNPs). The chemical reaction between maleimide and GDNPs was carried out at room temperature, under ambient atmosphere, and with minimal delay (few minutes) between i) exposure of the nanoparticles to the functional organic molecules and ii) washing/purification cycles subjected to the exposed GDNPs. The general procedure for the preparation of DNPs functionalized with maleimide derivatives is summarized in FIG. 2.

Characterization of the Functionalized DNPs—

Figure 3:
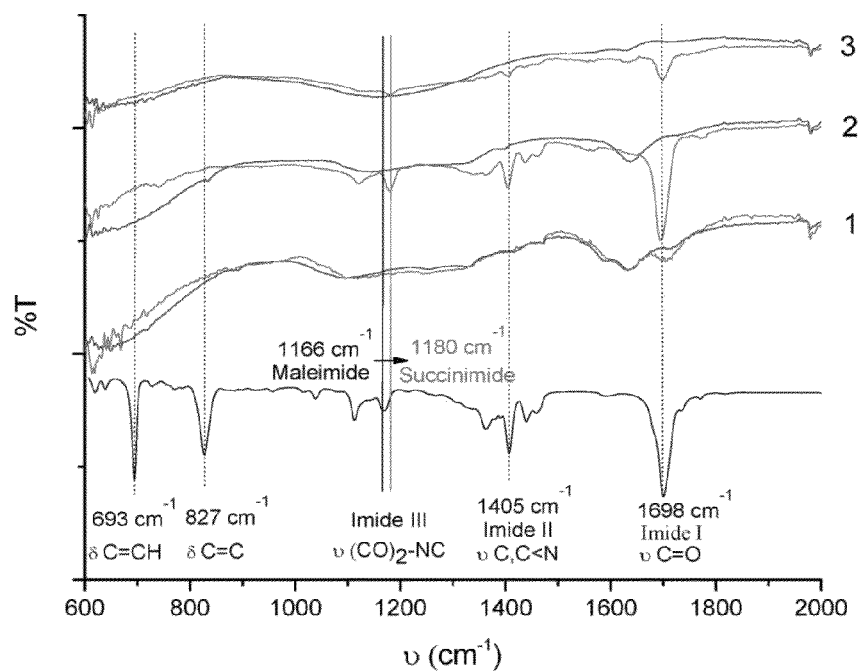
FIG. 3 is a set of FTIR spectra of the 2-ethyhexyl-substituted maleimide molecule alone, of the non-functionalized DNPs, and of the maleimide-functionalized DNPs: 1) Commercial DDNP, 2) DNPs annealed at 900° C. for 1 h (GDNPs), and 3) DNPs annealed at 1050° C. for 1 h.
Figure 4:
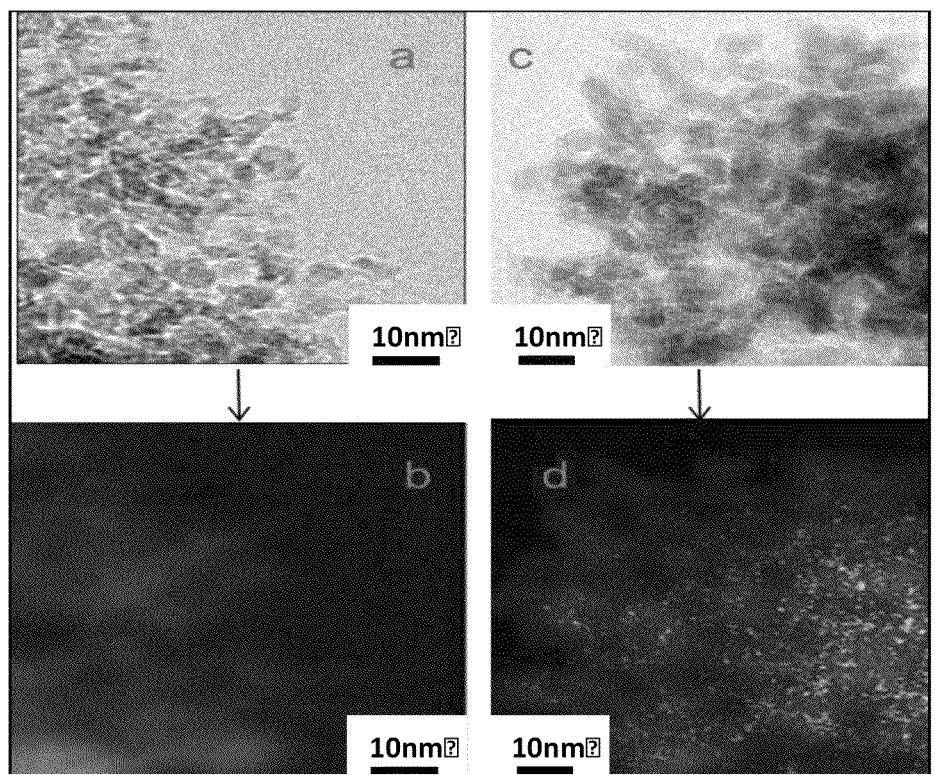
FIG. 4 is a set of micrographs (HRTEM) of a) non-functionalized GDNPs, and c) GDNPs exposed to the sulfur-containing maleimide derivative. Corresponding EELS map of carbon and sulfur elements for the b) non-functionalized GDNPs, and d) GDNPs exposed to the sulfur-containing maleimide derivative.

The nanoparticles exposed to maleimide were first characterized by FTIR (FIG. 3). This spectroscopic technique reveals that "lightly-graphitized" DNPs are more reactive towards maleimide than their non-annealed and their more graphitized counterparts. This is visible from the characteristic maleimide peaks which are most intense in FIG. 3 situation #2 (DNPs annealed at 900° C. and for 1 h). In addition, the loss of the C=C characteristic bands of maleimide, as well as the frequency-shifts observed for the other bands, are strong supporting evidences of i) the presence and ii) the chemical transformation of the maleimide molecule to its succinimide counterpart as it reacts with the GDNPs (FIG. 1).

The covalent functionalization of the maleimide derivative onto GDNPs was further supported by a control experiment in which the GDNPs were exposed to an analogous succinimide derivative (no reactive C=C), synthesized for the purpose of this control experiment, and exposed to GDNPs via the same protocol. Following this experiment, the succinimide derivative was not detected by FTIR after subjecting the exposed GDNPs to the standard washing cycles.

The solid-state NMR of the functionalized GDNPs was in agreement with the results generated by FTIR, showing no maleimide C=C characteristic peak, but a characteristic peak for succinimide (subsequent to the chemical transformation undergone by maleimide).

Figure III—FTIR spectra of the 2-ethyhexyl-substituted maleimide molecule alone (black curve), of the non-functionalized DNPs (blue curves), and of the maleimide-functionalized DNPs (red curves): 1) Commercial DDNP, 2) DNPs annealed at 900° C. for 1 h (GDNPs), and 3) DNPs annealed at 1050° C. for 1 h.

Importantly, FTIR revealed that the degree of surface functionalization is not appreciably affected by the duration of the exposition to the molecule, or by elevation of the reaction temperature. These experiments are additional supporting evidence of the spontaneous character of the reaction between GDNPs and the maleimide partner.

Next, the degree of surface functionalization of the functionalized GDNPs was estimated from the TGA data, and found to be 0.32 mmol·$g^{-1}$. This result is comparable to other results reported for various functionalization strategies in the literature. In support to the TGA analysis, the CHN elemental analysis of the functionalized nanoparticles was carried out, and found to be in excellent agreement with the TGA-estimated value.

Additional data in support of the effective functionalization taking place between GDNPs and maleimide were produced using a sulfur-containing maleimide derivative, synthesized with the purpose of labeling the GDNPs with a "marker" clearly observable by XPS and by Elemental HRTEM-EELS. The XPS analysis of the GDNPs exposed to the sulfur-containing maleimide derivative, and subsequently washed/purified following the same standard protocol as that used systematically for each new batch of DNPs, revealed the presence of a sulfur 2p peak. In contrast, a control XPS experiment with DDNPs revealed no detectable sulfur content. The HRTEM-EELS experiment carried out in parallel (FIG. 3) shows the detection of sulfur elements (detection of sulfur L-edge signal) present on the carbon surface of the GDNPs. In contrast, the control HRTEM-EELS experiment with DDNPs revealed no detectable sulfur content.

Other embodiments are within the scope of the following claims.

What is claimed is:

1. A method of making a functionalized diamond nanoparticle comprising exposing a diamond nanoparticle having surface diene moieties, nucleophilic moieties and/or dangling bonds to a dienophile to form a functionalized diamond nanoparticle product.

2. The method of claim 1, wherein exposing the diamond nanoparticle to the dienophile takes place at about ambient conditions, in the absence of catalyst and additional reagents.

3. The method of claim 1, wherein the dienophile is a cyclic imide, a furan, a pyrrole, a thiophene, or a cyclic anhydride.

4. The method of claim 1, wherein the dienophile is an acyclic alkene.

5. The method of claim 1, wherein the dienophile is a maleimide.

6. A compound of a formula (I) or (II):

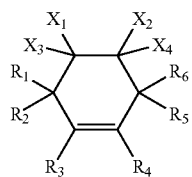
(I)

wherein each of $R_1$, $R_2$, $R_3$, $R_4$, $R_5$, or $R_6$, independently, are hydrogen or carbon atoms of a diamond nanoparticle, no more than two of $R_1$, $R_2$, $R_3$, $R_4$, $R_5$, or $R_6$ being hydrogen, each of $X_1$ and $X_2$, independently, is an electron withdrawing group, and each of $X_3$ and $X_4$, independently, is hydrogen, alkyl, an ester, amide, nitro, or nitrile or $X_3$ and $X_4$ together form a bond; or

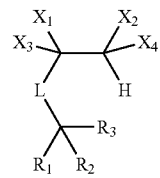
(II)

wherein each of $R_1$, $R_2$, or $R_3$, independently, are hydrogen or carbon atoms of a diamond nanoparticle, no more than one of $R_1$, $R_2$, or $R_3$, being hydrogen, each of $X_1$ and $X_2$, independently, is an electron withdrawing group, and each of $X_3$ and $X_4$, independently, is hydrogen, alkyl, an ester, amide, nitro, or nitrile or $X_3$ and $X_4$ together form a bond; and L is an oxo, thio or amino terminated linking group, or a bond, the linking group being a C2-C16 alkylene, arylene or aralkylene group the oxo, thio or amino group forming a bond with the carbon substituted by $X_1$ and $X_3$.

7. The compound of claim 6, wherein $X_3$ and $X_4$ together form a bond.

8. The compound of claim 6, wherein each of $X_3$ and $X_4$ are hydrogen.

9. The compound of claim 6, wherein the electron withdrawing group is an ester, amide, nitro, or nitrile.

10. The compound of claim 6, wherein each of $X_1$ and $X_2$ are an ester or amide.

11. The compound of claim 6, wherein each of $X_1$ and $X_2$ are an ester or amide and together can form a 5- to 8-membered ring.

12. A compound of claim 6, wherein the compound is of formula (I) and 2, 3, 4, 5, or 6 of $R_1$-$R_6$ are carbon atoms of the diamond nanoparticle.

13. A compound of claim 6, wherein the compound is a maleimide adduct of a diamond nanoparticle.

* * * * *